US00PP20831P2

(12) United States Plant Patent
Isobe et al.

(10) Patent No.: US PP20,831 P2
(45) Date of Patent: Mar. 16, 2010

(54) ***PETUNIA* PLANT NAMED 'SUNSURFCOPAVIO'**

(50) Latin Name: *Petunia×hybrida*
Varietal Denomination: Sunsurfcopavio

(75) Inventors: Yasuko Isobe, Shiga (JP); Takeshi Kanaya, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/284,880

(22) Filed: Sep. 22, 2008

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP19,132 P2 * 8/2008 Kleinhanns ..... Plt./356

* cited by examiner

*Primary Examiner*—Wendy C. Haas
(74) *Attorney, Agent, or Firm*—C. A. Whealy

(57) ABSTRACT

A new and distinct cultivar of *Petunia* plant named 'Sunsurfcopavio', characterized by its compact and mounding plant habit; vigorous growth habit; freely branching and flowering plant habit; long flowering period; dark purple violet-colored flowers; and good garden performance.

1 Drawing Sheet

Botanical designation: *Petunia×hybrida.*
Cultivar denomination: 'Sunsurfcopavio'.

BACKGROUND OF THE INVENTION

The present invention relates to a new and distinct cultivar of *Petunia*, botanically known as *Petunia×hybrida* and hereinafter referred to by the name 'Sunsurfcopavio'.

The new *Petunia* plant is a product of a planned breeding program conducted by the Inventors in Higashiomi, Shiga, Japan. The objective of the breeding program is to create new compact and mounding *Petunia* cultivars with freely branching habit and attractive flower coloration.

The new *Petunia* plant originated from a cross-pollination made by the Inventors in April, 2003 in Higashiomi, Shiga, Japan of a proprietary selection of *Petunia×hybrida* identified as code number PF4, not patented, as the female, or seed, parent with a proprietary selection of *Petunia×hybrida* identified as code number LV-01, not patented, as the male, or pollen, parent. The new *Petunia* was discovered and selected by the Inventors as a single flowering plant within the progeny of the stated cross-pollination in a controlled environment in Higashiomi, Shiga, Japan in September, 2005.

Asexual reproduction of the new *Petunia* plant by terminal cuttings in a controlled environment in Higashiomi, Shiga, Japan since October, 2005, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunsurfcopavio'. These characteristics in combination distinguish 'Sunsurfcopavio' as a new and distinct cultivar of *Petunia:*

1. Compact and mounding plant habit.
2. Vigorous growth habit.
3. Freely branching and flowering plant habit.
4. Long flowering period.
5. Dark purple violet-colored flowers.
6. Good garden performance.

Plants of the new *Petunia* can be compared to plants of the female parent selection. Plants of the new *Petunia* differ from plants of the female parent selection in the following characteristics:

1. Plants of the new *Petunia* are more compact and mounding than and not as trailing as plants of the female parent selection.
2. Plants of the new *Petunia* have smaller flowers than plants of the female parent selection.

Plants of the new *Petunia* can be compared to plants of the male parent selection. Plants of the new *Petunia* differ from plants of the male parent selection in the following characteristics:

1. Plants of the new *Petunia* are more compact and mounding than and not as upright as plants of the male parent selection.
2. Plants of the new *Petunia* have larger flowers than plants of the male parent selection.

Plants of the new *Petunia* can also be compared to plants of 'Keipabukas', disclosed in U.S. Plant Pat. No. 14,748. In side-by-side comparisons conducted in Higashiomi, Shiga, Japan, plants of the new *Petunia* and 'Keipabukas' differed in the following characteristics:

1. Plants of the new *Petunia* were more compact and mounding than plants of 'Keipabukas'.
2. Plants of the new *Petunia* had shorter internodes than plants of 'Keipabukas'.
3. Plants of the new *Petunia* had smaller leaves than plants of 'Keipabukas'.

4. Plants of the new *Petunia* had larger flowers than plants of 'Keipabukas'.
5. Flowers of plants of the new *Petunia* and 'Keipabukas' differed in color as flowers of plants of 'Keipabukas' had more violet-colored flowers.

BRIEF DESCRIPTION OF THE PHOTOGRAPHS

The accompanying colored photographs illustrate the overall appearance of the new *Petunia*, showing the colors as true as it is reasonably possible to obtain in colored reproductions of this type. Colors in the photographs may differ slightly from the color values cited in the detailed botanical description which accurately describe the colors of the new *Petunia*.

The photograph at the top of the sheet comprises a top perspective view of a typical flowering plant of 'Sunsurfcopavio' grown in a container.

The photograph at the bottom of the sheet is a close-up view of typical flowers, flower buds and leaves of 'Sunsurfcopavio'.

DETAILED BOTANICAL DESCRIPTION

The aforementioned photographs and following observations, measurements and values describe plants grown in Higashiomi, Shiga, Japan, under commercial practice during the spring in an outdoor nursery day temperatures averaging 23° C. and night temperatures averaging 13° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Petunia×hybrida* 'Sunsurfcopavio'.

Parentage:

*Female, or seed, parent.*—Proprietary selection of *Petunia×hybrida* identified as code number PF4, not patented.

*Male, or pollen, parent.*—Proprietary selection of *Petunia×hybrida* identified as code number LV-01, not patented.

Propagation:

*Type.*—By terminal cuttings.

*Time to initiate roots.*—About one week at temperatures of 20° C. to 25° C.

*Time to produce a rooted young plant.*—About three weeks at temperatures of 20° C. to 25° C.

*Root description.*—Fibrous; white in color.

*Rooting habit.*—Freely branching.

Plant description:

*Plant and growth habit.*—Compact and mounding plant habit. Freely branching habit with about 20 lateral branches developing per plant; pinching enhances lateral branch development. Vigorous growth habit.

*Plant height.*—About 12.2 cm.

*Plant diameter.*—About 28.6 cm.

Lateral branch description:

*Length.*—About 16.7 cm.

*Diameter.*—About 2.3 mm.

*Internode length.*—About 6 mm.

*Strength.*—Strong, flexible.

*Aspect.*—Upright to outwardly.

*Texture.*—Pubescent.

*Color.*—Close to 144B.

Foliage description:

*Arrangement.*—Alternate, simple.

*Length.*—About 4.1 cm.

*Width.*—About 1.9 cm.

*Shape.*—Elliptic.

*Apex.*—Broadly acute.

*Base.*—Obtuse.

*Margin.*—Entire.

*Texture, upper and lower surfaces.*—Pubescent.

*Venation pattern.*—Pinnate; reticulate.

*Color.*—Developing leaves, upper surface: Close to 137C. Developing leaves, lower surface: Close to 138B. Fully developed leaves, upper surface: Close to 137B; venation, close to 145B. Fully developed leaves, lower surface: Close to 138B; venation, close to 145B.

*Petioles.*—Length: About 0.7 mm. Diameter: About 2.1 mm. Texture, upper and lower surfaces: Sparsely pubescent. Color, upper and lower surfaces: Close to 145B.

Flower description:

*Flower arrangement and habit.*—Single salverform flowers arising from leaf axils. Freely flowering habit with usually about 15 open flowers per plant. Flowers face obliquely upright.

*Fragrance.*—Moderate, pleasant.

*Natural flowering season.*—Early flowering habit, plants of the new *Petunia* initiate and develop flowers about three to four weeks after planting. Long flowering period; flowering commences naturally during the spring and plants flower continuously throughout the summer until late autumn in Japan.

*Flower longevity.*—Individual flowers last about seven to ten days on the plant; flowers not persistent.

*Flower diameter.*—About 4.9 cm.

*Flower length (depth).*—About 4.4 cm.

*Throat diameter.*—About 9.5 mm.

*Tube diameter, base.*—About 2.3 mm.

*Tube length.*—About 2.5 cm.

*Flower bud.*—Shape: Cylindrical. Length: About 3.4 cm. Diameter: About 6.6 mm. Color: Close to 86B.

*Corolla.*—Arrangement: Five petals fused at the base and opening into a flared trumpet. Petal length from throat: About 2.1 cm. Petal width: About 2 cm. Petal shape: Spatulate. Petal apex: Mucronate. Petal margin: Entire. Petal texture, upper and lower surfaces: Smooth, glabrous; velvety. Throat texture: Smooth, glabrous. Tube texture: Pubescent. Color: Petal, when opening, upper surface: Close to 83A. Petal, when opening, lower surface: Close to 86B. Petal, fully opened, upper surface: Close to N81A. Petal, fully opened, lower surface: Close to N87A. Throat: Close to N87B; venation, close to N92C. Tube: Close to N87A.

*Calyx.*—Arrangement: One star-shaped calyx tube with five sepals fused at the base per flower. Sepal length: About 11.5 mm. Sepal width: About 2.8 mm. Sepal shape: Elliptic. Sepal apex: Acute. Sepal margin: Entire. Sepal texture, upper and lower surfaces: Pubescent. Color, upper surface: Close to 144A. Color, lower surface: Close to 144A; towards the base, close to N77B.

*Peduncles.*—Length: About 1.8 cm. Diameter: About 1.2 mm. Strength: Strong. Texture: Pubescent. Color: Close to 144C.

*Reproductive organs.*—Stamens: Quantity/arrangement: Five per flower. Stamen length: About 1.6 cm. Anther shape: Ellipsoidal. Anther size: About 1.9 mm by 2.3 mm. Anther color: Close to 85C. Pollen amount: Moderate. Pollen color: Close to 85B. Pistils: Quantity: One per flower. Pistil length: About 1.8 cm.

Style color: Close to 145C. Stigma shape: Transversely ellipsoidal. Stigma color: Close to 144B. Ovary color: Close to 143C. Seed/fruit: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen/pest resistance: Plants of the new *Petunia* have not been observed to be resistant to pests and pathogens common to *Petunia*.

It is claimed:

1. A new and distinct *Petunia* plant named 'Sunsurfcopavio' as illustrated and described.

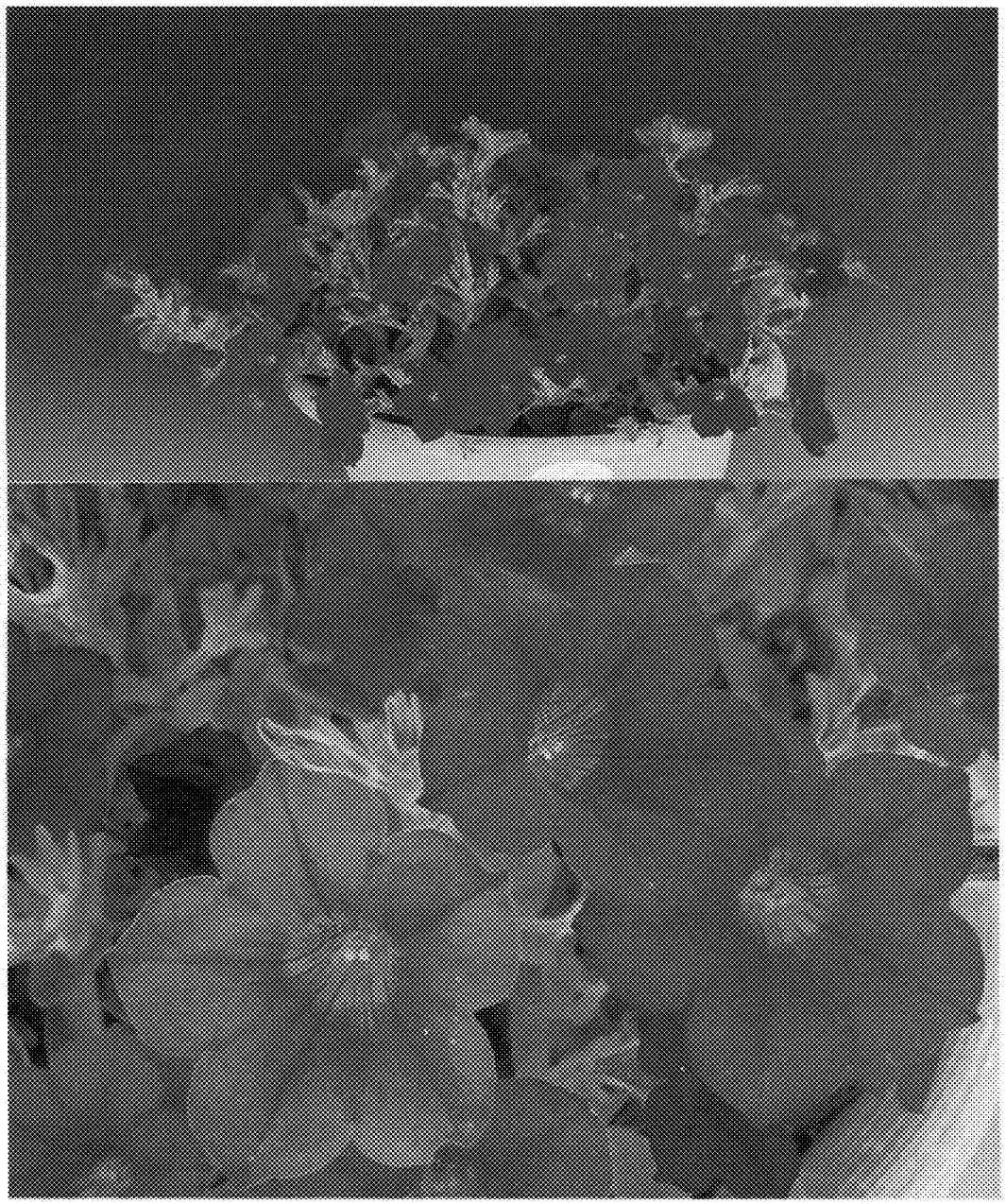

* * * * *